(12) United States Patent
Shen et al.

(10) Patent No.: US 10,507,090 B2
(45) Date of Patent: Dec. 17, 2019

(54) DENTAL ALL-CERAMIC RESTORATION AND MANUFACTURING METHOD THEREOF

(71) Applicant: HANGZHOU ERRAN Technology Co., Ltd., Zhejian (CN)

(72) Inventors: James Zhijian Shen, Zhejian (CN); Jing Zhao, Zhejian (CN)

(73) Assignee: Hangzhou Erran Technology Co., Ltd., Zhejian (CN)

( * ) Notice: Subject to any disclaimer, the term of this patent is extended or adjusted under 35 U.S.C. 154(b) by 0 days.

(21) Appl. No.: 15/503,149

(22) PCT Filed: Aug. 11, 2015

(86) PCT No.: PCT/CN2015/086670
§ 371 (c)(1),
(2) Date: Feb. 10, 2017

(87) PCT Pub. No.: WO2016/023470
PCT Pub. Date: Feb. 18, 2016

(65) Prior Publication Data
US 2017/0231730 A1 Aug. 17, 2017

(30) Foreign Application Priority Data

Aug. 12, 2014 (CN) .......................... 2014 1 0392647
Aug. 12, 2014 (CN) .......................... 2014 1 0392661

(51) Int. Cl.
*A61C 13/08* (2006.01)
*A61C 8/00* (2006.01)
(Continued)

(52) U.S. Cl.
CPC .............. *A61C 13/081* (2013.01); *A61C 5/20* (2017.02); *A61C 5/35* (2017.02); *A61C 5/77* (2017.02);
(Continued)

(58) Field of Classification Search
CPC ..... A61C 13/081; A61C 5/77; A61C 13/0004; A61C 13/0006; C04B 35/4885
See application file for complete search history.

(56) References Cited

U.S. PATENT DOCUMENTS 4,820,666 A * 4/1989 Hirano .................. C04B 35/119
501/104
6,495,073 B2 * 12/2002 Bodenmiller ...... A61C 13/0003
264/16

(Continued)

FOREIGN PATENT DOCUMENTS

CN 201676029 U 12/2010
CN 102302381 A 1/2012
(Continued)

OTHER PUBLICATIONS

CN 102755199 A (Peilong) Sep. 24, 2009 (English language machine translation). [online] [retrieved Dec. 12, 2018]. Retrieved from: Espacenet. (Year: 2009).*

(Continued)

*Primary Examiner* — Erin Snelting
(74) *Attorney, Agent, or Firm* — Burr & Forman LLP

(57) ABSTRACT

A dental all-ceramic restoration and manufacturing method thereof; the outer surface of the dental all-ceramic restoration has neither visible marks remaining from the removal of the connecting bars (7) nor local grinding traces and chipping, and is smooth with uniform structure. The manufacturing method thereof is wet-forming or milling. No connecting bars are needed to connect the dental restoration bodies (3) with a surrounding mould blank or ceramic blank. This eliminates the need for manually cutting off the connecting bars (7) to separate the forming body from the surrounding ceramic blank, further grinding and polishing process to treat the excessively rough outer surface, and thereby reducing the risk of chipping and premature failure.

(Continued)

In the manufacturing processes thereof, the hardened ceramic green body (2) made by wet-forming technique has more homogenous microstructure and less particle packing defects than the dry-pressed blanks and partially sintered blanks. Furthermore, higher surface smoothness can be obtained by milling unsintered hardened ceramic green body than by milling partially sintered blanks. The dental all-ceramic restoration has a high degree of surface finish, and can be directly used without polishing, veneering or glazing.

10 Claims, 4 Drawing Sheets

(51) Int. Cl.

| | | |
|---|---|---|
| A61C 13/00 | (2006.01) | |
| A61C 13/34 | (2006.01) | |
| A61K 6/02 | (2006.01) | |
| A61C 5/20 | (2017.01) | |
| A61C 5/35 | (2017.01) | |
| A61C 5/77 | (2017.01) | |
| A61C 13/271 | (2006.01) | |
| A61C 13/30 | (2006.01) | |

(52) U.S. Cl.
CPC .......... A61C 8/0012 (2013.01); A61C 8/0048 (2013.01); A61C 13/0004 (2013.01); A61C 13/0006 (2013.01); A61C 13/0022 (2013.01); A61C 13/0028 (2013.01); A61C 13/26 (2013.01); A61C 13/30 (2013.01); A61C 13/34 (2013.01); A61K 6/024 (2013.01); A61K 6/0205 (2013.01)

(56) References Cited

U.S. PATENT DOCUMENTS

| | | |
|---|---|---|
| 8,141,217 B2 | 3/2012 | Gubler et al. |
| 2005/0177266 A1 | 8/2005 | Kopelman et al. |
| 2005/0261795 A1 | 11/2005 | Ghosh et al. |
| 2007/0292822 A1 | 12/2007 | Stites |
| 2009/0059154 A1 | 3/2009 | Chuang et al. |
| 2009/0239199 A1* | 9/2009 | Cadario ............ A61C 13/0022 433/203.1 |
| 2010/0058588 A1 | 3/2010 | Heinz et al. |
| 2012/0143364 A1 | 6/2012 | Mcleod et al. |
| 2012/0148985 A1 | 6/2012 | Jung et al. |
| 2012/0175801 A1* | 7/2012 | Jahns ................ A61C 13/0003 264/19 |
| 2012/0282572 A1 | 11/2012 | MacLeod et al. |
| 2014/0272777 A1* | 9/2014 | Howe .................... A61C 13/12 433/49 |
| 2014/0272800 A1* | 9/2014 | Howe ................ A61C 13/0022 433/199.1 |
| 2015/0250568 A1* | 9/2015 | Fisker ................ A61C 13/0004 433/29 |
| 2017/0042647 A1* | 2/2017 | Burke ................ A61C 13/0019 |

FOREIGN PATENT DOCUMENTS

| | | | |
|---|---|---|---|
| CN | 102333498 A | | 1/2012 |
| CN | 102579148 A | | 7/2012 |
| CN | 102695471 A | | 9/2012 |
| CN | 102755199 A | * | 10/2012 |
| CN | 202682074 U | | 1/2013 |
| CN | 202682075 U | | 1/2013 |
| CN | 103083094 A | | 5/2013 |
| CN | 103479442 A | | 1/2014 |
| CN | 104434328 A | | 3/2015 |
| CN | 104434329 A | | 3/2015 |
| DE | 102005001600 | | 6/2006 |
| EP | 1066801 A1 | | 1/2001 |
| EP | 0824897 B1 | | 7/2001 |
| EP | 2470113 B1 | | 8/2013 |
| WO | 1999047065 A1 | | 9/1999 |
| WO | 2011023490 A1 | | 3/2011 |
| WO | 2014039268 A1 | | 3/2014 |

OTHER PUBLICATIONS

International Search Report and Written Opinion of PCT/CN2015/086670 dated Oct. 22, 2015, all enclosed pages cited.
English Translation of International Search Report and Written Opinion of PCT/CN2015/086670 dated Oct. 22, 2015, all enclosed pages cited.
Extended European Search Report of PCT/CN2015086670 dated Mar. 23, 2018, all enclosed pages cited.

* cited by examiner

DENTAL ALL-CERAMIC RESTORATION AND MANUFACTURING METHOD THEREOF

PRIORITY CLAIM

This application is a 35 U.S.C. § 371 national phase filing of International Patent Application No. PCT/CN2015/086670, filed on Aug. 11, 2015, through which and to which priority is claimed under 35 U.S.C. § 119 to Chinese Patent Application No. 201410392661.3, filed on Aug. 12, 2014, and Chinese Patent Application No. 201410392647.3, filed on Aug. 12, 2014.

TECHNICAL FIELD

The present invention relates generally to dental ceramic materials and engineering. Particularly, the present invention relates to a kind of dental all-ceramic restoration and the manufacturing method thereof.

BACKGROUND

In the 1970s, French dentist Dr. Duret introduced computer-aided design and computer-aided manufacturing (CAD/CAM) into the dental field. The principle of this technology as described in U.S. Pat. No. 4,742,464 is: "optical impression" is formed by collecting the three-dimensional reconstruction of tooth preparation via photo-electric devices; after inputting the optical impression into computer, "optical working model" is formed in the three-dimensional reconstruction software; by use of CAD software and careful adjustment, a "digital wax pattern" of the dental restoration is formed; finally, the data of the digital wax pattern as a control parameter is input to CNC milling machine, and then the pre-fixed blank is milled into the designed form; following the special treatment according to the characteristics of selected materials, the dental restoration with individual shape is finished. This invention reduces the reliance on the complicated manual techniques of manufacturing dental restorations which need to be accumulated over a long period of time, improves the accuracy and reliability of the dental restorations, and reduces the pains of patients brought by making impression of the wounded tissue. In recent years, with the rapid development of CAD/CAM technology and machinable restorative materials, especially the machinable ceramic materials, the development and the application of dental all-ceramic restorations are further promoted.

According to the different degree of density, machinable ceramic blanks can be divided into two categories. The one kind includes silicate-based glass and glass-ceramic, hard alumina and hard zirconia ceramic blanks. These prefabricated ceramic blanks are fixed onto the working table of CNC milling machine, and then the restorations are manufactured according to the digital wax pattern with equivalent ratio. The other kind includes porous alumina and zirconia ceramic blanks made by dry pressing and partially sintering. These prefabricated ceramic blanks are fixed onto the working table of CNC milling machine, and then the restoration bodies are manufactured according to the digital wax pattern with special enlarged ratio. After the second time sintering, the bodies become the final dense restorations. There are a number of patents related to the CAD/CAM manufacturing methods thereof, such as US20050261795 A1, EP0824897B1, CN201676029U, CN202682074U, CN202682075U, CN102579148A, et al.

In the CAD/CAM manufacturing methods thereof, in order to prevent restoration bodies from being gradually separated from the blanks with the reduction of the surrounding materials during processing, which could reduce the stability and precision of milling and even lead to the fracture of bodies, connecting bars (also called as support pillar, supporter, connector, tab, etc) on the outer surfaces of the bodies that connect to the surrounding blanks are necessary. After forming the dental restoration bodies, the technicians need to remove them from the residual blank manually by cutting the connecting bars, and then grinding the residual partial connecting bars and the surrounding area of connecting points on the outer surface of the bodies with a dental low-speed handpiece (as shown in FIG. 1). Manually grinding the connecting bars not only increases the technician's workload, reduces the advantages of automatic CAD/CAM technology, but also decreases the smoothness of the outer surface, which affects aesthetics, accelerates pigmentation and even discoloration on the surface, and causes excessive abrasion of adjacent teeth due to the rough surface. Therefore, grinding and polishing the outer surface of restorations is necessary after manually grinding of the connecting bars. Vibration during grinding may cause chipping on the thin parts of restorations, especially on the edge; and manually grinding introduces local stress and micro-defects to the surface of restoration, which reduces the long-term stability and reliability of the restorations, and even leads to premature fracture and restorative failure.

The reason of these drawbacks of the prior art is that both inner and outer surfaces of the dental restorations are formed simultaneously by milling the both surfaces of prefabricated blanks with multi-axis milling method. Thus, the use of connecting bars (also called as supporter, connecting bar, connector, linker, tab, etc.) is necessary. This is the common manufacturing method of these CAD/CAM technologies. As said in CN103479442A, before sintering the bodies of ceramic copings for both crown and bridge, connecting bars need to be manually cut off. As said in EP 2010061119 and CN 102695471A, 30 denture components are obtained after cutting off the tabs which connect the components with the solid blanks. The U.S. Pat. No. 8,141,217 B2 provides a prefabricated blank with large size. As FIG. 2 of this patent shows, connecting bars are used to connect the dental restoration bodies with the surrounding blank during processing. The patent US2009059154 invents a new kind of glass, glass-ceramic materials and dental components made therefrom. As FIG. 2b of this patent shows, connecting bars are used to connect the dental restoration bodies with the surrounding blank during processing. Therefore, grinding and polishing the outer surface of restorations is necessary after manually grinding of the connecting bars.

As described in CN102579148A and CN102302381A, zirconia restorations are separated from the ceramic blanks, and then the connecting bars on the outer surface are ground by a dental low-speed handpiece at the speed of 10000-20000 r/min. At the same time in order to improve the smoothness, the surface of the crown needs to be further ground.

Another common drawback of prior art is that the formed dental restorations can not be directly applied in clinic, and must be manually polished by technicians, and/or veneered, glazed before being applied. The reason of the above mentioned drawbacks is that the prefabricated ceramic blanks are dry. So the surface of the formed dental restorations are very rough, which not only affects aesthetics, but also leads to excessive abrasion of the opposite natural teeth during chewing (Oh W S, et al. Factors affecting enamel and ceramic wear: A literature review. J Prosthet Dent, 2002, 87 (4): 451-9; L. Wang, et al. Friction and wear behaviors of dental ceramics against natural tooth enamel, J Eur Ceram Soc, 2012, 32: 2599-2606). The Prefabricated ceramic blanks generally include unsintered green-bodies and partially sintered blanks. The unsintered green-bodies has plasticity, and a certain degree of plastic deformation can occur during processing to reduce the risk of accidental chipping. Ideally, the surface of dental restorations obtained by milling the green-bodies is smoother than that obtained by milling the partially sintered blanks. But since the plastic deformation is limited and the strength is insufficient of the complete dry green-bodies, they are difficult to sustain a large milling force and keep the integrity. This technique can not be realized. The mechanism of milling pre-sintered blanks is brittle delamination, because the granule sintering neck has been partially formed. The size and the form of debris are irregular and the milling process is not easy to be controlled. Thus the surface of dental restorations is very rough. However, due to the fact that the partially sintered ceramic blanks can resist a large milling force and the secondary sintering is relatively fast, the partially sintered ceramic blanks are normally used in prior art (Frank Thomas Filser. Direct Ceramic Machining of Ceramic Dental Restorations. 2001, p80-81; WO1999047065A1).

For reducing the negative effects of the rough surface of the formed dental restorations, dental technicians need to manually polish, glaze or veneer the restorations before application. All commonly used dry green body and partially sintered blanks have these drawbacks, no matter they are produced by dry pressing the ceramic powders or by wet-forming. As described in US20050261795A1, CN102579148A and CN102302381A, the fully sintered dental restorations need to be further polished or glazed.

Above all, the outer surface of the dental all-ceramic restorations produced by prior art is very rough, which must be polished, glazed or veneered to meet the requirements of surface smoothness. The dental all-ceramic restorations produced by prior art cannot obtain high smoothness and be directly used in clinical dental restorative treatment.

SUMMARY OF THE INVENTION

The present invention solves the technical problems of the prior art by providing a new kind of dental all-ceramic restoration and the manufacturing method thereof. The dental all-ceramic restoration provided by the present invention has neither visible marks remaining from the removal of the connecting bars nor local grinding traces and chipping on the outer surface, and the outer surface is smooth with uniform structure and high reliability. The dental all-ceramic restorations provided by the invention have high surface smoothness and can be directly applied in clinic without any polishing, glazing or veneering.

The manufacturing method thereof in present invention is not two-sided milling of the prefabricated ceramic blanks as the prior art, which completes forming in one step, but instead forming the restorations through step-by-step milling. No connecting bars are needed to connect the dental restoration bodies to the surrounding mould blank or ceramic blank. This eliminates the need for manually cutting off the connecting bars to separate the forming bodies and the surrounding blanks, and further grinding and polishing process to treat the excessively rough outer surface, thereby reducing the risk of chipping and premature failure.

I. Definition of Terms

"Surface smoothness", is to observe the degree of smoothness of the surface from the human visual point of view, which is represented by surface roughness.

"Coefficient of friction" is the ratio between the force necessary to move one surface horizontally over another and the pressure between the two surfaces, which is related to the surface roughness, independent of the size of the contact area.

"Dry-forming" refers to a kind of method in which the dry ceramic powder is dry-pressed to form green bodies, with or without the addition of a small amount of organic binder(s) to increase the particle packing density.

"Wet-forming" refers to a kind of method in which the packing density of ceramic particles is increased with the aid of liquid medium while achieving forming. When the addition of the amount of the liquid medium is small, ceramic powder can form a plastic green-body with good machinable properties by the aid of the liquid medium, and can further achieve the forming purpose by plastic deformation. Wet-forming usually requires a small amount of organic additives to ensure powder dispersion and the increase of the plasticity of the green body, which is well-known.

"Green body" refers to the ceramic body which is not sintered after formation. The physical characteristics of a green body is that no neck formation between individual ceramic particles could be found under the microscope. Green is always used to describe the state of un-sintered, such as green body, green blank/blank and so on.

"Hardened ceramic green body" refers to a ceramic green body which is strong enough to be treated by post-mechanical processing. Its strength is improved either by physical or chemical methods. Unlike the granule brittle delamination mechanism of milling the partially sintered body, the mechanism of milling the hardened ceramic green body includes also plastic deformation.

"Partially sintered body" refers to the ceramic body which is partially sintered after formation, but not being fully densified yet. The physical characteristics of a partially sintered body is that the neck formation between individual ceramic particles could be found under the microscope. Brown is often used to describe the state of the partially sintered, such as brown ceramic blank/blank, or directly described as presintered body, partially sintered body, soft sintered body and so on.

"Brittle delamination mechanism" refers to the brittle delamination of ceramic particles or their agglomerates during milling, leaving the surface with obvious traces and roughness.

"Plastic deformation mechanism" refers to the local plastic deformation which is introduced during milling, thereby improves the surface smoothness.

"Connecting bars" refers to the bars designed on the outer (axial) surface of the dental restorations in order to prevent the premature fracture with the reduction of the surround materials during milling. The design of bars are determined by the cutting force according to the material, cutting feed and speed. The connecting bar is also called as support pillar, supporter, connector, tab.

II. Technical Scheme Adopted by this Invention to Solve the Technical Problems

The present invention provides a kind of dental all-ceramic restoration, wherein the outer surface of the dental all-ceramic restoration has neither visible marks remaining from the removal of the connecting bars nor local grinding traces and chipping, and is smooth with uniform structure.

Furthermore, no connecting bar is needed to connect and fix the dental all-ceramic restoration of the present invention to the surrounding mould blank or ceramic blank during processing.

The present invention also provides manufacturing method thereof, comprising wet-forming method and milling method. No connecting bars are needed to connect and fix the dental all-ceramic restoration to the surrounding mould blank or ceramic blank during processing.

The wet-forming method refers to the manufacturing method thereof in the present invention, which differs from the usual forming method of the prefabricated blanks in the prior art, such as the forming method of glass, glass ceramics, ceramics, soft metals and so on. In the wet-forming process thereof, the hardened ceramic green body suitable for step-by-step milling maintains a certain degree of humidity. It overcomes the drawbacks of the complete dry green bodies in prior art that is not having sufficiently high strength and plasticity to sustain a large milling force to keep the integrity of the milling parts. The dental restorations produced from the hardened ceramic green body are smooth and the surface roughness of the natural surface without any manual treatment is comparable to that of the finely polished ones. The new kind of dental restoration can be applied directly in clinic, thus avoiding the manual grinding, polishing, glazing and veneering work by technicians in prior art.

In the manufacturing processes thereof, the hardened ceramic green body made by wet-forming has more homogenous microstructure and less particle packing defects than the dry-pressed and partially sintered blanks. Furthermore, higher surface smoothness can be obtained by milling unsintered hardened ceramic green body than by milling partially sintered blanks.

III. Different from the Prior Art, the Key Points on the Manufacturing Method of the Invention are 1. The dental all-ceramic restorations with the same form as the digital wax pattern are produced by step-by-step milling. No connecting bars are needed to connect the dental restoration bodies with the surrounding mould blank or ceramic blank. This eliminates the need for manually cutting off the connecting bars to separate the forming body and the surrounding ceramic blank, further grinding and polishing process to treat the excessive rough outer surface, and thereby reducing the risk of chipping and premature failure.

2. In the wet-forming process thereof, the hardened ceramic green body for step-by-step milling maintains a certain degree of humidity. It overcomes the drawbacks of the complete dry green bodies, which cannot sustain a large milling force or keep the integrity in the prior art due to the limitation of the strength and plastic deformation. The dental restorations produced with the hardened ceramic green body are smooth and their natural surface without any manual treatment have a surface roughness corresponding to the finely polished ones. They can be applied directly in clinic, to avoid the manual grinding, polishing, glazing and veneering work by technicians necessary in prior art.

3. In the manufacturing processes thereof, when the hardened ceramic green body is made by wet-forming technique, it has more homogenous microstructure and less particle packing defects than the dry-pressed blanks and partially sintered blanks. Furthermore, higher surface smoothness could be obtained by milling unsintered hardened ceramic green body than by milling partially sintered blanks in the prior art.

The first manufacturing method of this invention is wet-forming comprising the steps of:

step (1): Milling a mould blank to obtain a cavity mould having an inner surface corresponding to the outer surface form of the digital wax pattern or a convex mould having an outer surface corresponding to the inner surface form of the digital wax pattern;

step (2): Injecting the ceramic colloid into the cavity mould, or sealing the convex mould with a matched sleeve and then injecting the ceramic colloid into the shaping cavity between the sleeve and the convex mould. After being dried, the hardened ceramic green body with less than 10% liquid phase content is formed.

step (3): According to the inner surface form of the digital wax pattern, the outer surface form of the digital wax pattern, or the inner surface form combined with the partial outer surface of the digital wax pattern below the height of contour, milling the hardened ceramic green body to obtain the dental all-ceramic restoration body with the same form as the digital wax pattern;

Specifically, the wet-forming method comprises the following steps:

step (1): Milling mould blank to obtain a cavity mould having an inner surface corresponding to the outer surface form of the digital wax pattern or a convex mould having an outer surface corresponding to the inner surface form of the digital wax pattern.

step (2): Injecting the ceramic colloid into the cavity mould formed in step 1. or sealing the convex mould formed in step 1 with a matched sleeve and then injecting the ceramic colloid into the shaping cavity between the sleeve and the convex mould. After being dried, the hardened ceramic green body with less than 10% liquid phase content is formed.

step (3): According to the inner surface form of the digital wax pattern, or the inner surface form combined with the partial outer surface of the digital wax pattern below the height of contour, milling the hardened ceramic green body formed in the cavity mould to produce the dental all-ceramic restoration body with the same form as the digital wax pattern; or according to the outer surface form of the digital wax pattern, milling the hardened ceramic green body formed in the convex mould shaping cavity to produce the dental all-ceramic restoration body with the same form as the digital wax pattern.

By adopting the step (1) to (3), the dental all-ceramic restoration bodies with the same form as the digital wax patterns are produced. With the aid of step-by-step milling and wet-forming method, no connecting bars are needed to connect the dental restoration bodies with the surrounding mould blank or ceramic blank. Thus the outer surface of these bodies has neither visible marks remaining from the removal of the connecting bars nor local grinding traces and chipping, and the surface is smooth with uniform structure.

Preferably, one body or a plurality of bodies of the dental all-ceramic restorations can be manufactured simultaneously on a single mould blank and a hardened ceramic green body according to steps (1) to (3). For instance, a single mould blank said in step (1) could be used to produce one single dental crown, one single fixed partial denture with more than three units, a plurality of single dental crowns or a plurality of fixed partial dentures with more than three units.

Preferably, the cavity mould of step (1) is the cavity mould having an inner surface corresponding to the complete outer surface form of the digital wax pattern or corresponding to the partial outer surface form of the digital wax pattern;

Furthermore, during manufacturing the cavity mould, mentioned in step (1), having an inner surface corresponding to the partial outer surface form of the digital wax pattern, the part between the height of contour and incisal edge of anterior teeth or occlusal surface of posterior teeth, is milled according to the outer surface form of the digital wax pattern, whereas the other part between the height of contour and cervical margin is milled along the vertical line of the height of contour to mould blank without producing the undercut form below the height of contour.

Furthermore, the cavity mould having an outer surface form of the digital wax pattern and the convex mould having an inner surface form of the digital wax pattern in step (1) are produced by milling mould blanks by CNC milling machine; the hardened ceramic green body in step (3) is also milled by CNC milling machine.

Furthermore, the method of drying the ceramic colloid in step (2) is one or a plurality of methods selected from gel drying, osmotic drying, microwave drying, infrared drying, electrothermal drying, drying in an oven with infrared light or electric heating wire as a heat source, and drying agent. Preferably, the drying agent is one or a plurality of dessicants selected from quicklime, silica gel and porous silicates.

Preferably, before step (1) the manufacturing method further comprises the steps of: step A: tooth preparation; step B: making optical models of the dentitions; step C: generating the digital wax pattern of the all-ceramic dental restoration according to the optical models of the dentitions obtained in step B as the data source;

Preferably, after step (3) the manufacturing method further comprises the steps of: step D: removing the dental all-ceramic restoration body; step E: sintering the body thereof in a sintering furnace to form the dense dental all-ceramic restoration.

Further preferably, the step A, B and C before step (1) and the step D and E after step (3) are simultaneously comprised.

Preferably, within the step A, the tooth preparation is carried out according to the dental preparation principles for all-ceramic restorations; within the step B, the optical models of the dentitions include at least the prepared tooth, the adjacent teeth on both sides and the opposite teeth;

Preferably, the method of obtaining the optical models of the dentitions is selected from the one of following methods. The first option is to scan the impressions of dentitions taken in clinic, followed by transforming them into optical models via computer software. The second option is to take impressions of dentitions, make the plaster models, and then scan the plaster models to be the optical ones. The third option is to obtain the optical models by direct intraoral scanning of the dentitions. The dental impression may be scanned using a dental scanner. The computer software may be the dental CAD software. The dental intraoral scanner is used to directly scan the dentition.

Preferably, within the step C, the digital wax pattern of the dental all-ceramic restoration is designed by the dental restorative design software;

Preferably, within the step D, the method of removing the dental all-ceramic restoration body is to mill away the surrounding material of the mould blank to create a gap and then directly to take the body out by clamping or negative-pressure suction;

Preferably, within the step E, the sintering temperature is ranging from 1300° C. to 1600° C. with the holding time ranging from 0.1 h to 3 h.

Furthermore, within the manufacturing method of wet-forming, the material of the mould blank is one or a mixture of a plurality of the materials selected from the group consisting of gypsum, paraffin, epoxy, and polyethylene. Preferably, the porosity of the mould blank is 0% to 60% and preferably the porosity is 0% to 40%.

Furthermore, the ceramic colloid comprises solid phase component and liquid phase component. The solid phase component contains additive. The additive is PVA, PEG, or their mixture. The additive accounts for 0.5% to 5.0% of the solid phase component by weight, and more preferably the additive accounts for 1.0% to 3.0% by weight.

Preferably, the solid phase component accounts for 20% to 60% of the ceramic colloid by volume, and more preferably the solid phase component accounts for 25% to 35% by volume.

Preferably, the solid phase component is one or a mixture of a plurality of the ceramics selected from the group consisting of alumina, zirconia, spinel, garnet, and mullite; and more preferably the solid phase component is the mixture of 5% spinel and 95% zirconia, the mixture of 20% zirconia and 80% alumina, the mixture of 10% spinel and 90% alumina, or the mixture of 95% zirconia and 5% alumina, by weight.

Preferably, the liquid phase component is water, alcohols, or their mixture.

The second manufacturing method thereof is milling comprising the steps of:

(1) Milling the porous ceramic blank to obtain a cavity ceramic body having an inner surface corresponding to the inner surface form of the digital wax pattern, and milling the mould blank to obtain a convex mould having an outer surface corresponding to the inner surface form of the digital wax pattern; or milling the porous ceramic blank to obtain a convex ceramic body having an outer surface corresponding to the outer surface form of the digital wax pattern, and milling the mould blank to obtain a cavity mould having an inner surface corresponding to the outer surface form of the digital wax pattern.

(2) Matching and fixing the cavity ceramic body with the convex mould produced in step (1) together, or matching and fixing the convex ceramic body with the cavity mould produced in step (1) together.

(3) Milling the cavity ceramic body fixed with convex mould according to the outer surface form of digital wax pattern, to obtain the dental all-ceramic restoration body with the same form as the digital wax pattern; or milling the convex ceramic body fixed with cavity mould according to the inner surface form of the digital wax pattern, or the inner surface form combined with the partial outer surface of the digital wax pattern below the height of contour, to obtain the dental all-ceramic restoration body with the same form as the digital wax pattern.

By adopting the step (1) to (3), the dental all-ceramic restoration bodies with the same form as the digital wax patterns are produced. With the help of step-by-step milling method, no connecting bars are needed to connect the bodies with the surrounding mould blank or ceramic blank. Thus the outer surface of these bodies has neither visible marks remaining from the removal of the connecting bars nor local grinding traces and chipping, and the surface is smooth with uniform structure.

Preferably, one body or a plurality of bodies of dental all-ceramic restorations can be fabricated simultaneously on a single convex/cavity ceramic body fixed with the cavity/convex mould, respectively, according to steps (1) to (3). For instance, the single cavity/convex ceramic body with the matched convex/cavity mould said in step (1) could be used to produce one single dental crown or one single fixed partial denture with more than three units. Moreover, a plurality of cavity/convex moulds having different inner surface forms of digital wax patterns on one single ceramic body could be applied with the matched one single mould blank to produce a plurality of single dental crowns or fixed partial dentures with more than three units.

Furthermore, the cavity mould of step (1) having an inner surface corresponding to the partial outer surface form of the digital wax pattern; the convex ceramic body of step (1) having an outer surface corresponding to the complete outer surface form of digital wax pattern or the partial outer surface form of digital wax pattern.

Furthermore, during manufacturing the cavity mould and the convex ceramic body having partial outer surface form of the digital wax pattern of step (1), the part between the height of contour and incisal edge of anterior tooth or occlusal surface of posterior tooth is milled according to the outer surface form of the digital wax pattern, and the part between the height of contour and cervical margin is milled along the vertical line of the height of contour to the mould blank or ceramic blank without producing the undercut form below the height of contour.

That means the method for manufacturing the cavity mould having the partial outer surface form of the digital wax pattern inside is the same as that for the convex ceramic body having the partial outer surface form of the digital wax pattern.

Furthermore, wherein step (1) further comprises step (1)-A: milling the porous ceramic blank to obtain the cavity ceramic body having an inner surface corresponding to the inner surface form of the digital wax pattern.

Furthermore, wherein step (1) further comprises step (1)-B: milling the mould blank to obtain the convex mould having an outer surface corresponding to the inner surface form of the digital wax pattern.

Among them, the steps 1-A and 1-B may be arranged in any order.

Furthermore, wherein step (1) further comprises step (1)-C: Milling the mould blank to obtain a cavity mould having an inner surface corresponding to the partial outer surface form of the digital wax pattern to match the convex ceramic body. During manufacturing, the part between the height of contour and incisal edge of anterior tooth or occlusal surface of posterior tooth is milled according to the outer surface form of the digital wax pattern, whereas the other part between the height of contour and cervical margin is milled along the vertical line of the height of contour to the mould blank without producing the undercut form below the height of contour.

Furthermore, wherein step (1) further comprises step (1)-D: According to the complete outer surface form of the digital wax pattern or the partial outer surface form of the digital wax pattern in step (1)-C, milling the porous ceramic blank to obtain a convex ceramic body to match the cavity mould.

Among them, the steps 1-C and 1-D may be arranged in any order.

Furthermore, wherein milling process the milling is achieved by CNC milling machine. For example, within step 1 the milling of the porous ceramic or mould blank and in step 3 milling of the cavity or convex ceramic body can all be achieved by a CNC milling machine.

Furthermore, the method of fixing of step 2 is achieved by non-clip retention. The non-clip retention refers to any kind of fixture is not used between the restoration and the mould blank during processing, so as to avoid the fixture blocking the processing pathway.

Preferably, the non-clip retention method is vacuum retention or adhesive retention; more preferably, the adhesive used for the adhesive retention is wax, petrolatum or epoxy.

Preferably, before step (1) the manufacturing method further comprises the steps of: step A: tooth preparation; step B: making the optical models of the dentitions; step C: generating the digital wax pattern of the all-ceramic dental restoration according to the optical models of the dentitions obtained in step B as the data source;

Preferably, after step (3) the manufacturing method further comprises the following steps: step D: removing the dental all-ceramic restoration body; step E: sintering the body thereof in a sintering furnace to form the dense dental all-ceramic restoration.

Further preferably, the step A, B and C before step (1) and the step D and E after step (3) are simultaneously comprised.

Preferably, the step A, wherein tooth preparation is carried out according to the dental preparation principles for all-ceramic restorations;

Preferably, the step B, wherein the optical models of the dentitions include at least the prepared tooth, the adjacent teeth on both sides and the opposite teeth;

Preferably, the method of obtaining the optical models of the dentitions in step B is selected from one of the following methods. The first option is to scan the impressions of dentitions taken in clinic, followed by transforming them into optical models via computer software. The second option is to take impressions of dentitions in clinic, make the plaster models, and then scan the plaster models to obtain the optical ones. The third option is to obtain the optical models by direct intraoral scanning of the dentitions. The dental impression may be scanned using a dental scanner. The computer software may be the dental CAD software. The dental intraoral scanner is used to directly scan the dentition.

Preferably, the step C, wherein the digital wax pattern of the dental all-ceramic restoration is designed by the dental restorative design software;

Preferably, the step D, wherein the method of removing the dental all-ceramic restoration body is to mill away the surrounding material of the mould blank to create a gap and then to directly take the body out or to remove the body by negative-pressure suction. Adhesive can be melted by heating when necessary to avoid destroying the integrity of the dental all-ceramic restoration body;

Preferably, the step E, wherein the sintering temperature is ranging from 1300° C. to 1600° C. with the holding time ranging from 0.1 h to 3 h.

Furthermore, in the manufacturing method of milling, wherein the material of the mould blank is one or a mixture of a plurality of materials selected from the group consisting of gypsum, paraffin, epoxy and polyethylene.

Furthermore, the material of porous ceramic blank is one or a mixture of a plurality of ceramics selected from the group consisting of alumina, zirconia, spinel, garnet and mullite; and preferably the porous ceramic blank is the mixture of 5% spinel and 95% zirconia, the mixture of 20% zirconia and 80% alumina, or the mixture of 10% garnet and 90% alumina, by weight.

Furthermore, the porous ceramic blank is partially sintered dry-pressed blank or unsintered hardened ceramic green body;

Furthermore, the porosity of the said porous ceramic blank is 20% to 60%, preferably, the porosity is in the range of 30% to 50%.

The dental all-ceramic restorations of the present invention are veneering laminate, inlay, onlay, post, post and core, post-and-core crown, crown, bridge, implant, abutment, or upper structure of implant.

The present invention also provides the use of the new dental all-ceramic restorations, including dental restoration for both defect tooth and missing tooth and aesthetic restoration. Specifically the new dental all-ceramic restorations can be used in the fixed and removable restoration of both defect tooth and missing tooth, aesthetic restoration, minimally invasive dental restoration and in guided dental implantology. The dental all-ceramic restorations can be produced as veneering laminate, inlay, onlay, post, post and core, post-and-core crown, crown, bridge, implant, abutment, or upper structure of implant for dental restoration.

I. The Benefits of the Present Invention

1. The outer surface of the dental all-ceramic restorations has neither visible marks remaining from the removal of the connecting bars nor local grinding traces and chipping, it is smooth with uniform structure and high reliability.

2. The dental all-ceramic restorations with the same form as the digital wax pattern are produced by step-by-step milling method. No connecting bars are needed to connect the dental restoration bodies with the surrounding mould blank or ceramic blank. This eliminates the need for manually cutting off the connecting bars to separate the forming body and the surrounding ceramic blanks, and of any further grinding and polishing processes to treat the excessively rough outer surface, thereby reducing the risk of chipping and premature failure.

3. In the wet-forming process thereof, the hardened ceramic green body for step-by-step milling maintains a certain degree of humidity. It overcomes the drawbacks of the complete dry green bodies, which cannot sustain a large milling force or keep the integrity in prior art due to the limitation of the strength and plastic deformation. The dental restorations produced with the hardened ceramic green body are smooth and the surface roughness of the natural surface without any manually treatment is in correspondence to the finely polished ones in prior art. The new kind of dental restorations can be applied directly in clinic, to avoid the manual grinding, polishing, glazing and veneering work by technicians in the prior art.

4. In the manufacturing processes thereof, the hardened ceramic green body made by the wet-forming technique has more homogenous microstructure and less particle packing defects than the dry-pressed blanks and partially sintered blanks.

5. Higher surface smoothness can be obtained by milling unsintered hardened ceramic green body than by milling partially sintered blanks.

6. It is benefit to process thin cervical edge and improve the successful rate of the production by milling the hardened ceramic green bodies and partially sintered blanks with the support of the mould blanks.

7. The dental all-ceramic restorations of the present invention have high surface smoothness. The surface roughness (detected by scanning electron microscopy) is 50 nm to 300 nm and the coefficient of friction is ranging from 0.4 to 0.6.

In figures, 1, mould blank, 2, hardened ceramic green body, 3, dental all-ceramic restoration body, 4, sleeve, 5, sealing ring, 6, shaping cavity, 7, connecting bar, 8, porous ceramic blank.

DETAILED DESCRIPTION OF THE PREFERRED EMBODIMENT

The invention is explained in more detail below by means of the following illustrative non-limiting examples.

In the present invention, materials, equipments and the like, if not specifically described, are commercially available or are commonly used in the art. The methods in the following examples, unless specified, are conventional in the art.

Figure 1:
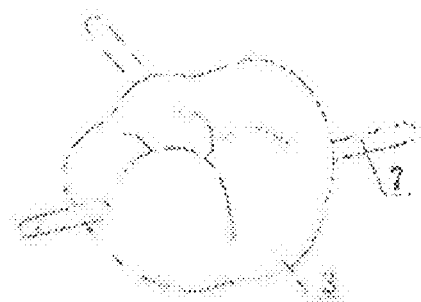
FIG. 1 is a schematic drawing of a dental all-ceramic restoration body (single crown) produced by the commonly used CAD/CAM manufacturing method.

FIG. 1 is a schematic drawing of a dental all-ceramic restoration body 3 (single crown) produced by the commonly used CAD/CAM manufacturing method. There are connecting bars 7 on the outer surface of the body thereof 3 to connect with the surrounding blank, which need to be manually ground after processing.

Figure 2:
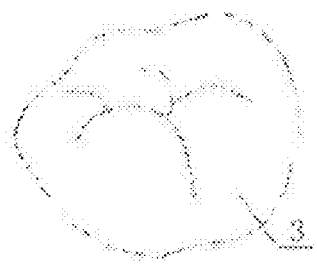
FIG. 2 is a schematic drawing of a dental all-ceramic restoration body (single crown) produced according to the present invention.

As shown in FIG. 2, no connecting bar 7 is needed to connect the dental restoration body 3 with the surrounding mould blank or ceramic blank. Thus the outer surface of the body thereof has neither visible marks remaining from the removal of the connecting bars nor local grinding traces and chipping, and the surface is smooth with uniform structure.

The wet-forming method of the present invention to produce the dental all-ceramic restorations comprises the steps of:

Step 1: Tooth preparation according to the dental preparation principles for all-ceramic restorations.

Step 2: Making the optical models of the dentitions include at least the prepared tooth, the adjacent teeth on both sides and the opposite teeth, to ensure that the final restoration is matchable to the real dentition morphology in oral, and restore the adjacent relationship and occlusal function.

Step 3: Generating the digital wax pattern of the all-ceramic dental restoration according to the optical model of the dentition obtained in step 2 as the data source by dental restorative design software. An enlargement ratio was considered corresponding to the sintering shrinkage rate of the ceramic.

Step 4: Milling mould blank to obtain a cavity mould having an outer surface form of the digital wax pattern or a convex mould having an inner surface form of the digital wax pattern by CNC milling machine. A single mould blank could be used to produce one single dental crown, one single fixed partial denture with more than three units, a plurality of single dental crowns or a plurality of fixed partial dentures with more than three units.

Step 5: Injecting the ceramic colloid into the cavity mould, or sealing the convex mould with a matched sleeve and then injecting the ceramic colloid into the shaping cavity between the sleeve and the convex mould. After being dried, the hardened ceramic green body with less than 10% liquid phase content is formed.

Step 6: According to the inner surface form of the digital wax pattern, the outer surface form of the digital wax pattern, or the inner surface form combined with the partial outer surface of the digital wax pattern below the height of contour, milling the hardened ceramic green body to obtain the dental all-ceramic restoration body with the same form as the digital wax pattern.

Step 7: Removing the dental all-ceramic restoration body.

Step 8: Sintering the body thereof in a sintering furnace to form the dense dental all-ceramic restoration.

Preferably, one body or a plurality of bodies of the dental all-ceramic restorations can be fabricated simultaneously on a single mould blank and a hardened ceramic green body according to steps (4) to (6). For instance, a single mould blank could be used to produce one single dental crown, one single fixed partial denture with more than three units, a plurality of single dental crowns or a plurality of fixed partial dentures with more than three units.

EXAMPLE 1

For the case and restorative plan: A defect posterior tooth was planed to be restored with a zirconia ceramic single crown.

Figure 3:
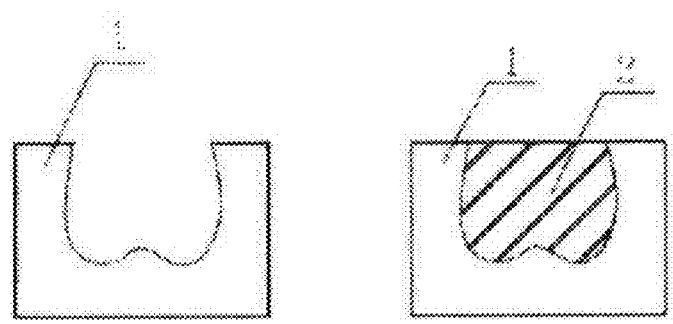
FIG. 3 is a schematic drawing of the steps of the wet-forming manufacturing method thereof according to the present invention.
Figure 3:
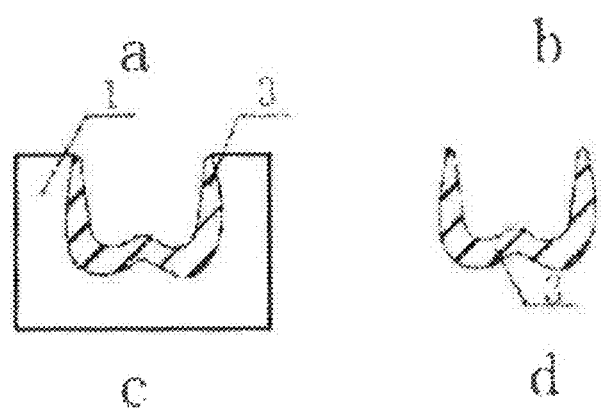

As shown in FIG. 3, the wet-forming manufacturing method of the dental all-ceramic restoration comprising the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. An enlargement ratio was considered corresponding to the sintering shrinkage rate of the ceramic.

Step 4: Milling the mould blank 1 (gypsum blank, porosity 20%) to obtain a cavity mould having a complete outer surface form of the digital wax pattern by CNC milling machine (FIG. 3a).

Step 5: Injecting the ceramic colloid into the cavity mould. The ceramic colloid comprises a solid phase component and a liquid phase component, wherein the solid phase component, which was zirconia, accounted for 50% of the ceramic colloid by volume, and the liquid phase component was water. The hardened ceramic green body 2 was obtained after being osmotic dried to with 9 wt % liquid phase content (FIG. 3b).

Step 6: According to the inner surface form of the digital wax pattern, milling the hardened ceramic green body by CNC milling machine to obtain the dental all-ceramic restoration body 3 with the same form as the digital wax pattern (FIG. 3c).

Step 7: Milling away the surrounding material of the mould blank 1 to create a gap and then taking the body out by negative-pressure suction (FIG. 3d).

Step 8: Sintering the body at 1300° C. for 2 h to form the dense dental all-ceramic crown with smooth surface. The heating rate was 5~10° C./min and cooling was furnace cooling.

EXAMPLE 2

For the case and restorative plan: A defect posterior tooth was planned to be restored with a zirconia/alumina ceramic single crown.

As shown in FIG. 3, the wet-forming manufacturing method of the dental all-ceramic restoration comprising the steps of:

Step 1: Tooth preparation according to the dental preparation principle for zirconia/alumina all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Taking the impressions of the upper and the lower dentitions in clinic and then scanning them with 3 Shape D810 scanner. Transforming them into optical models via 3 Shape DentalDesigner™ software.

Step 3: Generating the digital wax pattern of the all-ceramic dental restoration according to the optical models of the dentitions obtained in step 2 as the data source by 3 Shape DentalDesigner™ software. An enlargement ratio was considered corresponding to the sintering shrinkage rate of the ceramic.

Step 4: Milling the mould blank 1 (paraffin blank, porosity 0%) to obtain a cavity mould having a complete outer surface form of the digital wax pattern by CNC milling machine (FIG. 3a).

Step 5: Injecting the ceramic colloid into the cavity mould. The ceramic colloid comprised solid phase component and liquid phase component, wherein the solid phase component, which was the mixture of 20 wt % zirconia and 80 wt % alumina, accounted for 20% of the ceramic colloid by volume, and the liquid phase component was 90% ethanol aqueous solution. The hardened ceramic green body 2 was obtained after being gel dried to with 4 wt % liquid phase content (FIG. 3b), Step 6: According to the inner surface form of the digital wax pattern, milling the hardened ceramic green body by CNC milling machine to obtain of the dental all-ceramic restoration body 3 with the same form as the digital wax pattern (FIG. 3c).

Step 7: Milling the surrounding material of the mould blank 1 to create a gap and then taking the body out by negative-pressure suction (FIG. 3d).

Step 8: Sintering the body at 1400° C. for 3 h to form the dense dental all-ceramic crown with smooth surface. The heating rate was 5~10° C./min and cooling was furnace cooling.

EXAMPLE 3

For the case and restorative plan: A defect posterior tooth was planned to be restored with an alumina ceramic single crown.

Figure 4:
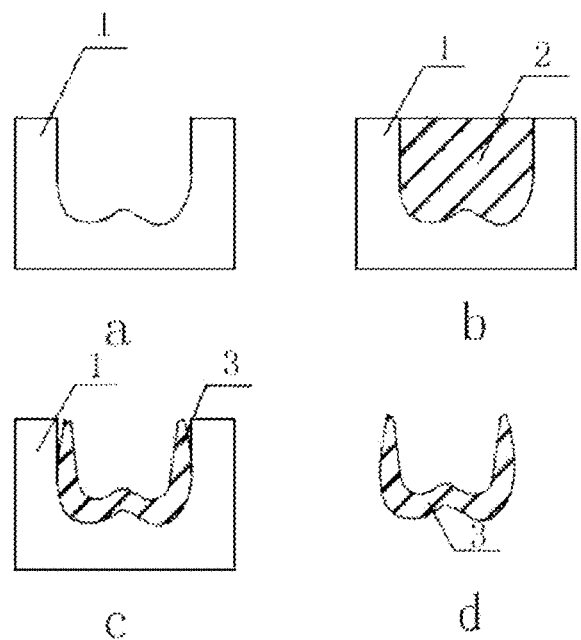
FIG. 4 is a schematic drawing of the steps of the other wet-forming manufacturing method thereof according to the present invention.

As shown in FIG. 4, the wet-forming manufacturing method of the dental all-ceramic restoration comprising the steps of:

Step 1: Tooth preparation according to the dental preparation principle for alumina all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: Milling the mould blank 1 (polyethylene blank, porosity 60%) to obtain the cavity mould having an inner surface corresponding to the partial outer surface form of the digital wax pattern by CNC milling machine. During processing, the part between the height of contour and occlusal surface, was milled according to the outer surface form of the digital wax pattern, whereas the other part between the height of contour and cervical margin was milled along the vertical line of the height of contour to the mould blank without producing the undercut form below the height of contour (FIG. 4a).

Step 5: Injecting the ceramic colloid into the cavity mould. The ceramic colloid comprised a solid phase component and a liquid phase component, wherein the solid phase component, which was alumina, accounted for 60% of the ceramic colloid by volume, and the liquid phase component was anhydrous alcohol. The hardened ceramic green body 2 was obtained after being osmotic dried by polyethylene and further dried with electric heating oven to with 5 wt % liquid phase content (FIG. 4b), Step 6: According to the inner surface form combined with the partial outer surface of the digital wax pattern below the height of contour, milling the hardened ceramic green body by CNC milling machine to obtain of the dental all-ceramic restoration body 3 with the same form as the digital wax pattern (FIG. 4c).

Step 7: Milling the surrounding material of the mould blank 1 to create a gap and then directly taking the body out by clamping (FIG. 4d).

Step 8: Sintering the body at 1600° C. for 0.1 h to form the dense dental all-ceramic crown with smooth surface. The heating rate was 5~10° C./min and cooling was furnace cooling.

EXAMPLE 4

For the case and restorative plan: A defect posterior tooth was planned to be restored with a zirconia-alumina ceramic composite single crown.

As shown in FIG. 4, the wet-forming manufacturing method of the dental all-ceramic restoration comprising the steps of:

Step 1: Tooth preparation according to the dental preparation principle for zirconia/alumina all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Taking the impressions of the upper and the lower dentitions in clinic and then scanning them with 3 Shape D810 scanner. Transforming them into optical models via 3 Shape DentalDesigner™ software.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: Milling the mould blank 1 (gypsum blank, porosity 20%) to obtain the cavity mould having an inner surface corresponding to the partial outer surface form of the digital wax pattern by CNC milling machine. During processing, the part between the height of contour and occlusal surface, was milled according to the outer surface form of the digital wax pattern, whereas the other part between the height of contour and cervical margin was milled along the vertical line of the height of contour to mould blank without producing the undercut form below the height of contour (FIG. 4a).

Step 5: Injecting the ceramic colloid into the cavity mould. The ceramic colloid comprised a solid phase component and a liquid phase component, wherein the solid phase component, which was the mixture of 20 wt % zirconia and 80 wt % alumina, accounted for 20% of the ceramic colloid by volume, and the liquid phase component was 90% ethanol aqueous solution. The hardened ceramic green body 2 was obtained after being dried by microwave oven to with less than 10 wt % liquid phase content (FIG. 4b).

Step 6: According to the inner surface form combined with the partial outer surface of the digital wax pattern below the height of contour, milling the hardened ceramic green body by CNC milling machine to obtain the dental all-ceramic restoration body 3 with the same form as the digital wax pattern (FIG. 4c).

Step 7: Milling the surrounding material of the mould blank 1 to create a gap and then directly taking the body out by clamping (FIG. 4d).

Step 8: Sintering the body at 1400° C. for 3 h to form the dense dental all-ceramic crown with smooth surface. The heating rate was 5~10° C./min and cooling was furnace cooling.

EXAMPLE 5

For the case and restorative plan: A defect posterior tooth was planned to be restored with a zirconia-alumina ceramic composite single crown.

Figure 5:
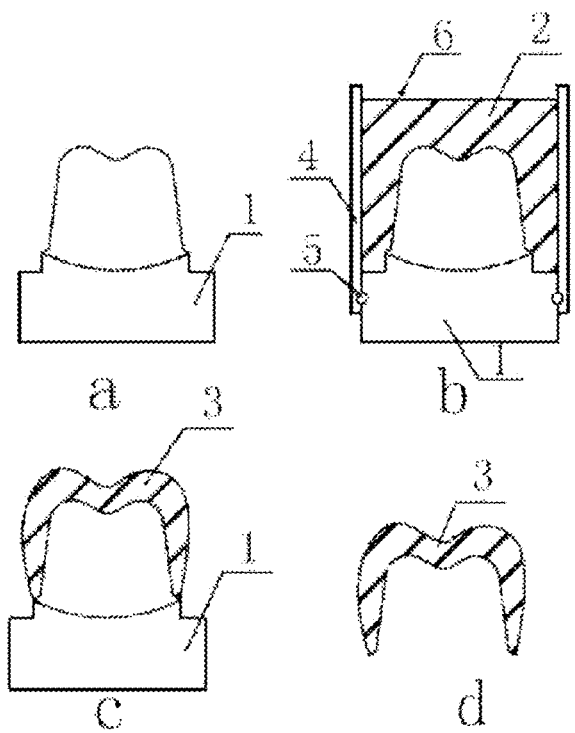
FIG. 5 is a schematic drawing of the steps of the other wet-forming manufacturing method thereof according to the present invention.

As shown in FIG. 5, the wet-forming manufacturing method of the dental all-ceramic restoration comprising the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: Milling mould blank 1 (paraffin blank, porosity 0%) to obtain a convex mould having an inner surface form of the digital wax pattern by CNC milling machine (FIG. 5a).

Step 5: Sealing the convex mould 1 with a matched sleeve 4 by sealing ring 5, and then injecting the ceramic colloid into the shaping cavity 6 between the sleeve and the convex mould. The ceramic colloid comprised solid phase component and liquid phase component, wherein the solid phase component, which was the mixture of 95 wt % zirconia and 5 wt % alumina, accounted for 50% of the ceramic colloid by volume, and the liquid phase component was water. The hardened ceramic green body 2 was obtained after being gel dried to with 3 wt % liquid phase content (FIG. 5b).

Step 6: According to the outer surface form of the digital wax pattern, milling the hardened ceramic green body to obtain the dental all-ceramic restoration body 3 with the same form as the digital wax pattern (FIG. 5c)

Step 7: Milling the surrounding material of the mould blank 1 to create a gap and then taking the body out by negative-pressure suction (FIG. 5d).

Step 8: Sintering the body at 1400° C. for 3 h to form the dense dental all-ceramic crown with smooth surface. The heating rate was 5~10° C./min and cooling was furnace cooling.

EXAMPLE 6

For the case and restorative plan: A defect posterior tooth was planned to be restored with an alumina ceramic single crown.

As shown in FIG. 5, the wet-forming manufacturing method of the dental all-ceramic restoration comprising the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: Milling mould blank 1 (epoxy blank, porosity 60%) to obtain a convex mould having an inner surface form of the digital wax pattern by CNC milling machine (FIG. 5a).

Step 5: Sealing the convex mould 1 with a matched sleeve 4 by sealing ring 5, and then injecting the ceramic colloid into the shaping cavity 6 between the sleeve and the convex mould. The ceramic colloid comprised solid phase component and liquid phase component, wherein the solid phase component, which was alumina, accounted for 60% of the ceramic colloid by volume, and the liquid phase component was 90% ethanol aqueous solution. The hardened ceramic green body 2 was obtained after being gel dried to with 5 wt % liquid phase content (FIG. 5b).

Step 6: According to the outer surface form of the digital wax pattern, milling the hardened ceramic green body to obtain the dental all-ceramic restoration body 3 with the same form as the digital wax pattern (FIG. 5c)

Step 7: Milling the surrounding material of the mould blank 1 to create a gap and then directly taking the body out by clamping (FIG. 5d).

Step 8: Sintering the body at 1600° C. for 0.1 h to form the dense dental all-ceramic restoration with smooth surface. The heating rate was 5~10° C./min and cooling was furnace cooling.

EXAMPLE 7

For the case and restorative plan: Aesthetic restoration of anterior teeth was planned by use of spinel ceramic veneering laminates.

In reference to steps 1-8 of Example 6 and FIG. 5, the differences of the wet-forming method for veneering laminates from the method described in Example 6 were:

Step 1: Tooth preparation according to the dental preparation principle for all-ceramic veneering laminates.

Step 4: The material of mould blank 1 was the mixture of gypsum and paraffin, which porosity was 40% (FIG. 5a).

Step 5: The ceramic colloid comprised a solid phase component and a liquid phase component, wherein the solid phase component, which was spinel ceramic, accounted for 25% of the ceramic colloid by volume, and the liquid phase component was 90% ethanol aqueous solution (FIG. 5b).

Step 8: Sintering the body at 1400° C. for 2 h to form the dense dental all-ceramic veneering laminates with smooth surface. The heating rate was 5~10° C./min and cooling was furnace cooling.

EXAMPLE 8

For the case and restorative plan: Tooth defect of premolar was planned to be restored with garnet ceramic inlay.

In reference to steps 1-8 of Example 6 and FIG. 5, the differences of the wet-forming method for inlay from the method described in Example 6 were:

Step 1: Tooth preparation according to the dental preparation principle for all-ceramic inlay.

Step 4: The material of mould blank 1 was the mixture of gypsum and epoxy, which porosity was 20% (FIG. 5a).

Step 5: The ceramic colloid comprised a solid phase component and a liquid phase component, wherein the solid phase component, which was garnet ceramic, accounted for 35% of the ceramic colloid by volume. The solid phase component contained the mixture of PVA and PEG as additive, which accounted for 1.0 wt % of the solid phase component. The liquid phase component was 90% ethanol aqueous solution (FIG. 5b).

Step 8: Sintering the body at 1300° C. for 0.1 h to form the dense dental all-ceramic inlay with smooth surface. The heating rate was 5~10° C./min and cooling was furnace cooling.

EXAMPLE 9

For the case and restorative plan: Tooth defect of premolar was planned to be restored with mullite ceramic onlay.

In reference to steps 1-8 of Example 6 and FIG. 5, the differences of the wet-forming method for onlay from the method described in Example 6 were:

Step 1: Tooth preparation according to the dental preparation principle for all-ceramic onlay.

Step 4: The material of mould blank 1 was the mixture of gypsum and epoxy, which porosity was 20% (FIG. 5a).

Step 5: The ceramic colloid comprised a solid phase component and a liquid phase component, wherein the solid phase component, which was mullite ceramic, accounted for 30% of the ceramic colloid by volume. The solid phase component contained the mixture of PVA and PEG as additive, which accounted for 5.0 wt % of the solid phase component. The liquid phase component was 90% ethanol aqueous solution (FIG. 5b).

Step 8: Sintering the body at 1300° C. for 1 h to form the dense dental all-ceramic restoration with smooth surface. The heating rate was 5~10° C./min and cooling was furnace cooling.

EXAMPLE 10

For the case and restorative plan: Serious tooth defect of RCT-ed premolar was planned to be restored with spinel-zirconia ceramic composite post and core.

In reference to steps 1-8 of Example 6 and FIG. 5, the differences of the wet-forming method for post and core from the method described in Example 6 are:

Step 1: Tooth preparation according to the dental preparation principle for all-ceramic post and core.

Step 4: The material of mould blank 1 was paraffin, which porosity was 0% (FIG. 5a).

Step 5: The ceramic colloid comprised a solid phase component and a liquid phase component, wherein the solid phase component, which was the mixture of 5% spinel and 95% zirconia, accounted for 20% of the ceramic colloid by volume. The solid phase component contained PEG as additive, which accounted for 5.0 wt % of the solid phase component. The liquid phase component was water (FIG. 5b). Step 8: Sintering the body at 1400° C. for 2 h to form the dense dental all-ceramic post and core with smooth surface. The heating rate was 5~10° C./min and cooling was furnace cooling.

EXAMPLE 11

For the case and restorative plan: Serious tooth defect of RCT-ed mandibular anterior tooth was planned to be restored with spinel-alumina ceramic composite post-and-core crown.

In reference to steps 1-8 of Example 6 and FIG. 5, the differences of the wet-forming method for post-and-core crown from the method described in Example 6 were:

Step 1: Tooth preparation according to the dental preparation principle for all-ceramic post-and-core crown.

Step 4: The material of mould blank 1 was paraffin, which porosity was 0% (FIG. 5a).

Step 5: The ceramic colloid comprised a solid phase component and a liquid phase component, wherein the solid phase component, which was the mixture of 10 wt % spinel and 90 wt % alumina, accounted for 60% of the ceramic colloid by volume. The solid phase component contained PVA as additive, which accounted for 3.0 wt % of the solid phase component. The liquid phase component was water (FIG. 5b).

Step 8: Sintering the body at 1600° C. for 0.1 h to form the dense dental all-ceramic post-and-core crown with smooth surface. The heating rate was 5~10° C./min and cooling was furnace cooling.

The milling method of the present invention for manufacturing ceramic restorations comprises two options.

The first option comprises the steps of:

Step 1: Tooth preparation according to the dental preparation principle for all-ceramic restorations.

Step 2: Making the optical models of the dentitions include at least the prepared tooth, the adjacent teeth on both sides and the opposite teeth, to ensure that the final restoration is matchable to the real dentition morphology in oral, and can restore the adjacent relationship and occlusal function.

Step 3: Generating the digital wax pattern of the all-ceramic dental restoration according to the optical models of the dentitions obtained in step 2 as the data source by dental restorative design software. An enlargement ratio is considered corresponding to the sintering shrinkage rate of the ceramic.

Step 4: Milling the porous ceramic blank to obtain a cavity ceramic body having an inner surface corresponding to the inner surface form of the digital wax pattern by CNC milling machine. The porous ceramic blank is partially sintered dry-pressed blank or unsintered hardened ceramic green body.

Step 5: Milling the mould blank to obtain a convex mould having an outer surface corresponding to the inner surface form of the digital wax pattern by CNC milling machine.

Step 6: Transferring the cavity ceramic body produced in step 4 onto the convex mould produced in step 5, and fixing them together by non-clamp retention method. The retention force needs to be strong enough to avoid vibration, displacement and even drop of ceramic body during processing.

Step 7: According to the outer surface form of the digital wax pattern, milling the cavity ceramic body fixed with convex mould to obtain the dental all-ceramic restoration body with the same form as the digital wax pattern Step 8: Removing the dental all-ceramic restoration body from the convex mould.

Step 9: The body thereof is sintered in a sintering furnace to form the dense dental all-ceramic restoration with smooth surface.

The second option comprises the steps of:

Step 1: Tooth preparation according to the dental preparation principle for all-ceramic restorations.

Step 2: Making the optical models of the dentitions include at least the prepared tooth, the adjacent teeth on both sides and the opposite teeth, to ensure that the final restoration is matchable to the real dentition morphology in oral, and restore the adjacent relationship and occlusal function.

Step 3: Generating the digital wax pattern of the all-ceramic dental restoration according to the optical models of the dentitions obtained in step 2 as the data source by dental restorative design software. An enlargement ratio is considered corresponding to the sintering shrinkage rate of the ceramic.

Step 4: According to the outer surface form of the digital wax pattern, milling the mould blank to obtain a cavity mould having partial outer surface form of the digital wax pattern by CNC milling machine. During processing, the part between the height of contour and incisal edge of anterior teeth or occlusal surface of posterior teeth is milled according to the outer surface form of the digital wax pattern, whereas the part between the height of contour and cervical margin is milled along the vertical line of the height of contour to mould blank without producing the undercut form below the height of contour.

Step 5: According to the complete outer surface form of the digital wax pattern or the partial outer surface as described in Step 4, milling the porous ceramic blank to obtain a convex ceramic body having complete outer surface form of the digital wax pattern or partial outer surface form of the digital wax pattern by CNC milling machine.

Step 6: Transferring the cavity mould produced in step 4 onto the convex ceramic body in step 5, and fixing them together by non-clamp retention method. The retention force needs to be strong enough to avoid vibration, displacement and even drop of ceramic body during processing.

Step 7: According to the inner surface form of the digital wax pattern or the inner surface form combined with the partial outer surface of the digital wax pattern below the height of contour, milling the convex ceramic body fixed with cavity mould to obtain the dental all-ceramic restoration body with the same form as the digital wax pattern.

Step 8: Removing the dental all-ceramic restoration body from the cavity mould.

Step 9: The body thereof is sintered in a sintering furnace to form the dense dental all-ceramic restoration with smooth surface.

In the step 4 and 5 described in both options, the single cavity/convex ceramic body with the matched convex/cavity mould could be used to produce one single dental crown or one single fixed partial denture with more than three units. Moreover, a plurality of cavity/convex moulds having different inner surface forms of the digital wax patterns on one single ceramic body could be applied with the matched one single mould blank to produce a plurality of single dental crowns or fixed partial dentures with more than three units.

In the step 8 described in both options, the method of removing the dental all-ceramic restoration body is to mill away the surrounding material of mould blank to create a gap and then to directly take the body out by clamping or by negative-pressure suction. Adhesion can be melted by heating when necessary to avoid destroying the integrity of the body.

Preferably, one body or a plurality of bodies of dental all-ceramic restorations can be fabricated simultaneously on a single convex ceramic body or a cavity ceramic body fixed with the convex mould or cavity mould, respectively, according to steps 4 to 6. For instance, the single cavity/convex ceramic body with the matched convex/cavity mould said in step 4 and 5 could be used to produce one single dental crown or one single fixed partial denture with more than three units. Moreover, a plurality of cavity/convex moulds having different inner surface forms of the digital wax patterns on one single ceramic body could be applied with the matched one single mould blank to produce a plurality of single dental crowns or fixed partial dentures with more than three units.

The milling method of the present invention is explained in more detail below by means of the following illustrative non-limiting examples.

EXAMPLE 12

For the case and restorative plan: A defect posterior tooth was planned to be restored with a zirconia ceramic single crown.

Figure 6:
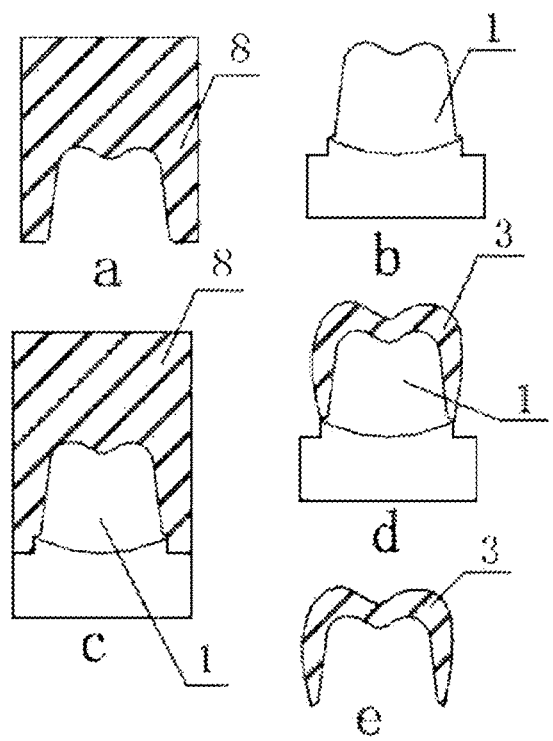
FIG. 6 is a schematic drawing of the steps of the milling manufacturing method thereof according to the present invention.

As shown in FIG. 6, the milling method for manufacturing the dental all-ceramic restoration comprises the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: Milling the porous ceramic blank 8 to obtain a cavity ceramic body having an inner surface corresponding to the inner surface form of the digital wax pattern by CNC milling machine. The porous ceramic blank 8 was partially sintered dry-pressed zirconia blank with porosity of 20% (FIG. 6a). Step 5: Milling the mould blank 1 to obtain a convex mould having an outer surface corresponding to the inner surface form of the digital wax pattern by CNC milling machine. The mould blank 1 was gypsum (FIG. 6b).

Step 6: Transferring the cavity ceramic body produced in step 4 onto the convex mould produced in step 5, and fixing them together by vacuum retention (FIG. 6c).

Step 7: According to the outer surface form of the digital wax pattern, milling the cavity ceramic body fixed with convex mould to obtain the dental all-ceramic restoration body 3 with the same form as the digital wax pattern (FIG. 6d).

Step 8: Removing the body 3 from the convex mould (FIG. 6e).

Step 9: Sintering the body at 1300° C. for 2 h to form the dense dental all-ceramic crown with smooth surface. The heating rate was 5~10° C./min and cooling was furnace cooling.

EXAMPLE 13

For the case and restorative plan: A defect posterior tooth was planned to be restored with a zirconia-alumina ceramic composite single crown.

As shown in FIG. 6, the milling method for manufacturing the dental all-ceramic restoration comprises the steps of:

Step 1: Tooth preparation according to the dental preparation principle for zirconia/alumina all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Taking the impressions of the upper and the lower dentitions in clinic and then scanning them with 3 Shape D810 scanner. Transforming them into optical models via 3 Shape DentalDesigner™ software.

Step 3: Generating the digital wax pattern of the all-ceramic dental restoration according to the optical models of the dentitions obtained in step 2 as the data source by 3 Shape DentalDesigner™ software. An enlargement ratio was considered corresponding to the sintering shrinkage rate of the ceramic.

Step 4: Milling the porous ceramic blank 8, to obtain a cavity ceramic body having an inner surface corresponding to the inner surface form of the digital wax pattern by CNC milling machine. The porous ceramic blank 8 was unsintered hardened ceramic green body comprising the mixture of 20 wt % zirconia and 80 wt % alumina with porosity of 60% (FIG. 6a).

Step 5: Milling the mould blank 1 to obtain a convex mould having an outer surface corresponding to the inner surface form of the digital wax pattern by CNC milling machine. The mould blank 1 was paraffin (FIG. 6*b*).

Step 6: Transferring the cavity ceramic body produced in step 4 onto the convex mould produced in step 5, and fixing them together by adhesion retention. The adhesive was wax (FIG. 6*c*).

Step 7: According to the outer surface form of the digital wax pattern, milling the cavity ceramic body fixed with convex mould to obtain the dental all-ceramic restoration body 3 with the same form as the digital wax pattern (FIG. 6*d*).

Step 8: Removing the body 3 from the convex mould (FIG. 6*e*).

Step 9: Sintering the body at 1400° C. for 3 h to form the dense dental all-ceramic crown with smooth surface. The heating rate was 5~10° C./min and cooling was furnace cooling.

EXAMPLE 14

For the case and restorative plan: A defect posterior tooth was planned to be restored with a zirconia/alumina ceramic single crown.

Figure 7:
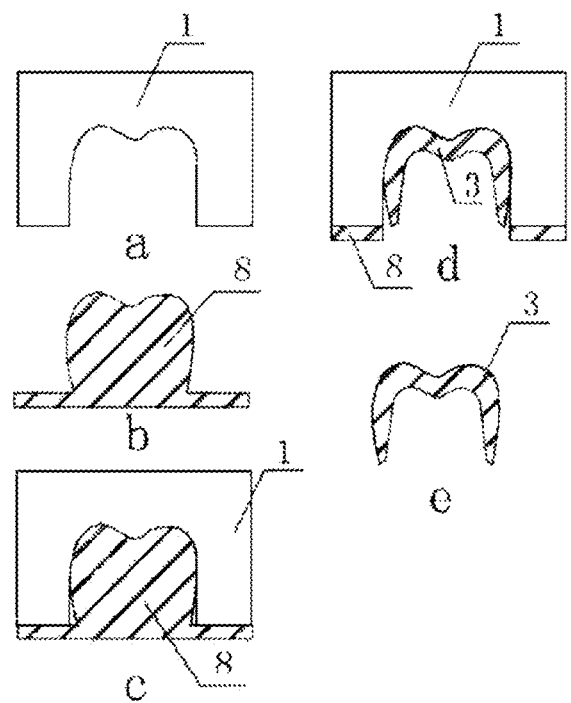
FIG. 7 is a schematic drawing of the steps of the other milling manufacturing method thereof according to the present invention.

As shown in FIG. 7, the milling method for manufacturing the dental all-ceramic restoration comprises the steps of:

Step 1: Tooth preparation according to the dental preparation principle for zirconia/alumina all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Taking the impressions of the upper and the lower dentitions in clinic and then scanning them with 3 Shape D810 scanner. Transforming them into optical models via 3 Shape DentalDesigner™ software.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: According to the outer surface form of the digital wax pattern, milling the mould blank 1 to obtain a cavity mould having partial outer surface form of the digital wax pattern by CNC milling machine. During processing, the part between the height of contour and occlusal surface was milled according to the outer surface form of the digital wax pattern, whereas the part between the height of contour and cervical margin was milled along the vertical line of the height of contour to mould blank without producing the undercut form below the height of contour. The material of mould blank 1 was gypsum (FIG. 7*a*).

Step 5: According to the complete outer surface form of the digital wax pattern, milling the porous ceramic blank 8 to obtain a convex ceramic body having complete outer surface form of digital wax pattern by CNC milling machine. The porous ceramic blank 8 was unsintered hardened ceramic green body comprising the mixture of 20 wt % zirconia and 80 wt % alumina with porosity of 60% (FIG. 7*b*)

Step 6: Transferring the cavity mould produced in step 4 onto the convex ceramic body in step 5, and fixing them together by adhesion retention method. The adhesive was petrolatum (FIG. 7*c*).

Step 7: According to the inner surface form of the digital wax pattern, milling the convex ceramic body to obtain the dental all-ceramic restoration body with the same form as the digital wax pattern (FIG. 7*d*).

Step 8: Removing the body 3 from the cavity mould (FIG. 7*e*).

Step 9: Sintering the body at 1400° C. for 3 h to form the dense dental all-ceramic crown with smooth surface. The heating rate was 5~10° C./min and cooling was furnace cooling.

EXAMPLE 15

For the case and restorative plan: A defect posterior tooth was planned to be restored with a zirconia ceramic single crown.

As shown in FIG. 7, the milling method for manufacturing the dental all-ceramic restoration comprises the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: According to the outer surface form of the digital wax pattern, milling the mould blank 1 to obtain a cavity mould having partial outer surface form of the digital wax pattern by CNC milling machine. During processing, the part between the height of contour and occlusal surface was milled according to the outer surface form of the digital wax pattern, whereas the part between the height of contour and cervical margin was milled along the vertical line of the height of contour to mould blank without producing the undercut form below the height of contour. The material of mould blank 1 was paraffin (FIG. 7*a*).

Step 5: According to the complete outer surface form of the digital wax pattern, milling the porous ceramic blank 8 to obtain a convex ceramic body having complete outer surface form of the digital wax pattern by CNC milling machine. The porous ceramic blank 8 was partially sintered dry-pressed zirconia blank with porosity of 50% (FIG. 7*b*).

Step 6: Transferring the cavity mould produced in step 4 onto the convex ceramic body in step 5, and fixing them together by vacuum retention (FIG. 7*c*).

Step 7: According to the inner surface form of the digital wax pattern, milling the convex ceramic body to obtain the dental all-ceramic restoration body with the same form as the digital wax pattern (FIG. 7*d*).

Step 8: Removing the body 3 from the cavity mould (FIG. 7*e*).

Step 9: Sintering the body at 1300° C. for 2 h to form the dense dental all-ceramic crown with smooth surface. The heating rate was 5~10° C./min and cooling was furnace cooling.

EXAMPLE 16

For the case and restorative plan: A defect posterior tooth was planned to be restored with a spinel/zirconia ceramic single crown.

Figure 8:
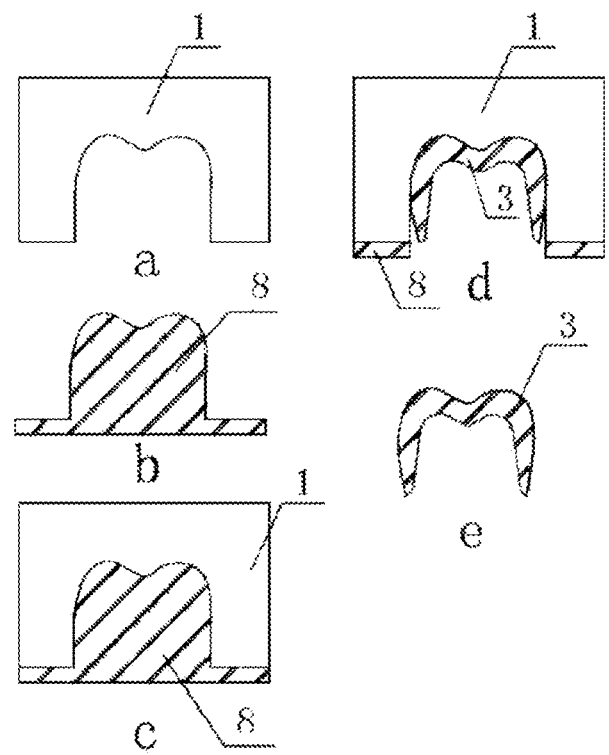
FIG. 8 is a schematic drawing of the steps of the other milling manufacturing method thereof according to the present invention.

As shown in FIG. 8, the milling method for manufacturing the dental all-ceramic restoration comprises the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: According to the outer surface form of the digital wax pattern, milling the mould blank 1 to obtain a cavity mould having partial outer surface form of the digital wax pattern by CNC milling machine. During processing, the part between the height of contour and occlusal surface was milled according to the outer surface form of the digital wax pattern, whereas the part between the height of contour and cervical margin was milled along the vertical line of the height of contour to mould blank without producing the undercut form below the height of contour. The material of mould blank 1 was epoxy (FIG. 8*a*).

Step 5: According to the partial outer surface form of digital wax pattern, milling the porous ceramic blank 8 to obtain a convex ceramic body having partial outer surface form of digital wax pattern by CNC milling machine. The porous ceramic blank 8 was unsintered hardened ceramic green body comprising the mixture of 5 wt % spinel and 95 wt % zirconia with porosity of 40% (FIG. 8*b*).

Step 6: Transferring the cavity mould produced in step 4 onto the convex ceramic body in step 5, and fixing them together by adhesion retention. The adhesive was petrolatum (FIG. 8*c*).

Step 7: According to the inner surface form combined with the partial outer surface of the digital wax pattern below the height of contour, milling the convex ceramic body to obtain the dental all-ceramic restoration body 3 with the same form as the digital wax pattern (FIG. 8*d*).

Step 8: Removing the body 3 from the cavity mould (FIG. 8*e*).

Step 9: Sintering the body at 1400° C. for 2 h to form the dense dental all-ceramic restoration with smooth surface. The heating rate was 5~10° C./min and cooling was furnace cooling.

EXAMPLE 17

For the case and restorative plan: A defect posterior tooth was planned to be restored with a garnet/alumina ceramic single crown.

As shown in FIG. 8, the milling method for manufacturing the dental all-ceramic restoration comprises the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: According to the outer surface form of the digital wax pattern, milling the mould blank 1 to obtain a cavity mould having partial outer surface form of the digital wax pattern by CNC milling machine. During processing, the part between the height of contour and occlusal surface was milled according to the outer surface form of the digital wax pattern, whereas the part between the height of contour and cervical margin was milled along the vertical line of the height of contour to mould blank without producing the undercut form below the height of contour. The material of mould blank 1 was epoxy (FIG. 8*a*).

Step 5: According to the partial outer surface form of the digital wax pattern, milling the porous ceramic blank 8 to obtain a convex ceramic body having partial outer surface form of the digital wax pattern by CNC milling machine. The porous ceramic blank 8 was unsintered hardened ceramic green body comprising the mixture of 10 wt % garnet and 90 wt % alumina with porosity of 40% (FIG. 8*b*).

Step 6: Transferring the cavity mould produced in step 4 onto the convex ceramic body in step 5, and fixing them together by adhesion retention. The adhesive was epoxy (FIG. 8*c*).

Step 7: According to the inner surface form combined with the partial outer surface of the digital wax pattern below the height of contour, milling the convex ceramic body to obtain the dental all-ceramic restoration body 3 with the same form as the digital wax pattern (FIG. 8*d*).

Step 8: Removing the body 3 from the cavity mould (FIG. 8*e*).

Step 9: Sintering the body at 1600° C. for 0.1 h to form the dense dental all-ceramic restoration with smooth surface. The heating rate was 5~10° C./min and cooling was furnace cooling.

EXAMPLE 18

For the case and restorative plan: A defect posterior tooth was planned to be restored with an alumina ceramic single crown.

As shown in FIG. 8, the milling method for manufacturing the dental all-ceramic restoration comprises the steps of:

Step 1: Tooth preparation according to the dental preparation principle for all-ceramic crown. Occlusal reduction 1.0 mm~1.5 mm, axial surface reduction 0.8~1.0 mm, shoulder width 0.3~0.5 mm, axial divergent degree of 6~8°, rounded point angle and line angle.

Step 2: Making the optical models by directly scanning the upper and the lower dentitions with 3 Shape TROIS intra-oral scanner.

Step 3: Generating the digital wax pattern of the all-ceramic dental restoration according to the optical models of the dentitions obtained in step 2 as the data source by 3 Shape DentalDesigner™ software. A certain enlarge ratio was considered corresponding to the sintering shrinkage rate of the ceramic.

Step 4: According to the outer surface form of the digital wax pattern, milling the porous ceramic blank 8 to obtain a convex ceramic body having partial outer surface form of the digital wax pattern by CNC milling machine. During processing, the part between the height of contour and occlusal surface was milled according to the outer surface form of the digital wax pattern, whereas the part between the height of contour and cervical margin was milled along the vertical line of the height of contour to ceramic blank without producing the undercut form below the height of contour. The porous ceramic blank 8 was unsintered hardened alumina ceramic green body with porosity of 30% (FIG. 8*b*).

Step 5: According to the partial outer surface form of the digital wax pattern, milling the mould blank 1 to obtain a cavity mould having partial outer surface form of the digital wax pattern by CNC milling machine. The material of mould blank 1 was polyethylene (FIG. 8*a*).

Step 6: Transferring the cavity mould produced in step 5 onto the convex ceramic body in step 4, and fixing them together by adhesion retention. The adhesive was epoxy (FIG. 8*c*).

Step 7: According to the inner surface form combined with the partial outer surface of the digital wax pattern below the height of contour, milling the convex ceramic body to obtain the dental all-ceramic restoration body with the same form as the digital wax pattern (FIG. 8*d*).

Step 8: Removing the body 3 from the cavity mould (FIG. 8*e*).

Step 9: Sintering the body at 1600° C. for 0.1 h to form the dense dental all-ceramic crown with smooth surface. The heating rate was 5~10° C./min and cooling was furnace cooling.

EXAMPLE 19

For the case and restorative plan: Tooth loss of mandibular anterior tooth was planned to be restored with spinel fixed partial denture.

In reference to steps 1-9 of Example 17 and FIG. 8, the differences of the milling method for fixed partial denture from the method described in Example 17 were:

Step 1: Tooth preparation according to the dental preparation principle for all-ceramic fixed partial denture.

Step 4: The material of mould blank 1 was the mixture of polyethylene and paraffin (FIG. 8*a*).

Step 5: The porous ceramic blank 8 was unsintered hardened spinel ceramic green body with porosity of 40% (FIG. 8*b*).

Step 9: Sintering the body at 1400° C. for 2 h to form the dense dental all-ceramic restoration with smooth surface. The heating rate was 5~10° C./min and cooling was furnace cooling.

EXAMPLE 20

For the case and restorative plan: Tooth loss of mandibular anterior tooth was planned to be restored by implantation. After healing, a garnet ceramic abutment was produced.

In reference to steps 2-9 of Example 17 and FIG. 8 (no tooth preparation is needed for implantation, thus the step is eliminated), the differences of the milling method for abutment from the method described in Example 17 were:

Step 4: The material of mould blank 1 was the mixture of gypsum and paraffin (FIG. 8*a*).

Step 5: The porous ceramic blank 8 was unsintered hardened garnet ceramic green body with porosity of 40% (FIG. 8*b* ).

Step 9: Sintering the body at 1300° C. for 0.1 h to form the dense dental all-ceramic abutment with smooth surface. The heating rate was 5~10° C./min and cooling was furnace cooling.

Example 21

For the case and restorative plan: Tooth loss of mandibular anterior tooth was planned to be restored by implantation. After healing, a mullite ceramic upper structure of implant was produced.

In reference to steps 2-9 of Example 17 and FIG. 8 (no tooth preparation is needed for implantation, thus the step is eliminated), the differences of the milling method for upper structure of implant from the method described in Example 17 were:

Step 4: The material of mould blank 1 was the mixture of gypsum and epoxy (FIG. 8*a*).

Step 5: The porous ceramic blank 8 was unsintered hardened mullite ceramic green body with porosity of 40% (FIG. 8*b*).

Step 9: Sintering the body at 1300° C. for 1 h to form the dense dental all-ceramic upper structure of implant with smooth surface. The heating rate was 5~10° C./min and cooling was furnace cooling.

COMPARATIVE EXAMPLE 1

To evaluate the surface smoothness/roughness of the dental all-ceramic restorations produced in Example 1 to 21 of the present invention and thereof produced according to the prior art by scanning electron microscopy and the coefficient of friction.

Sample preparation: premolars without obvious wear scar, extracted for orthodontic demand, were collected from 13 to 15 years old young persons. Each tooth was embedded in epoxy resin after pulpless, with the enamel of buccal surface (at least 5×5 mm area) exposed. The enamel surface was then grounded by carborundum sand paper in water, gradually from 300 to 2000 mesh.

Friction pair preparation comprising the steps of: (1) Samples 1-21: the dental all-ceramic restorations produced in Example 1 to 21 were by the wet-forming method and the milling method according to the present invention; (2) Sample 22: the dental all-ceramic restoration was produced by milling the dry partially sintered zirconia ceramic blank (commercially available) and then being fully sintered according to the prior art; (3) Sample 23: was the one further polished by 1 μm diamond powder based on Sample 22; (4) Sample 24: was the one further glazed based on Sample 22; (5) Sample 25: the dental all-ceramic restoration was produced by milling the dry lithium disilicate glass ceramic blank (commercially available) and then being fully sintered according to the prior art.

Friction and wear test: the wear pairs of the plates of natural teeth and friction pair of four kinds of dental all-ceramic restorations were tested by a micro friction and wear testing apparatus under the artificial saliva. The test was under vertical load 4 N, and cyclic friction with back-and-forth movement pattern. Every enamel sample was tested with four different restorations, each for 5000 cycles, at frequency 2 Hz and sliding displacement 1 mm.

Characterization of the worn surfaces: The wear scars on the worn surfaces of teeth enamel and on that of the antagonist restoration were investigated by a scanning electron microscope. The widths of worn scars were also measured. The coefficient of friction between the enamel and the restoration was calculated according to the relationship between the surface friction and the displacement under different cycles in the test.

Result was shown in the following table:

| Sample | Surface Roughness (nm) | Coefficient of Friction |
|---|---|---|
| Sample 1-11 | 50-200 | 0.4-0.6 |
| Sample 12, 15 | 100-300 | 0.5-0.6 |

-continued

| Sample | Surface Roughness (nm) | Coefficient of Friction |
|---|---|---|
| Sample 13, 14, 16-21 | 100-200 | 0.4-0.6 |
| Sample 22 | 1000-3000 | 0.7-0.8 |
| Sample 23 | 50-100 | 0.48-0.5 |
| Sample 24 | 50-100 | 0.6-0.7 |
| Sample 25 | 1000-6000 | 0.65-0.7 |

It can be seen from the table that the surfaces of the restorations produced by milling the dried pre-sintered zirconia ceramic blank (sample 22) and the lithium disilicate glass ceramic blank (sample 25) were very rough. The surface roughness of both was greater than 1000 nm, and the coefficient of friction of both was greater than 0.6, which was much higher than those of the dental restorations (Samples 1-21) produced by the wet-forming and milling methods of the present invention. Sample 22 and Sample 25 must be finely polished and glazed to reduce surface roughness, but the glazed surface did not effectively reduce the friction coefficient, which had potential risks of excessive wear on the natural teeth. However, Samples 1-21 had similar surface smoothness as the finely polished and glazed samples without any surface treatments, which met the clinical application requirements.

COMPARATIVE EXAMPLE 2

To evaluate the appearance and the microstructure of the dental all-ceramic restorations produced by wet-forming method according to the present invention and thereof produced by milling dry partially sintered zirconia blanks according to the prior art.

Figures 9A, 9B:
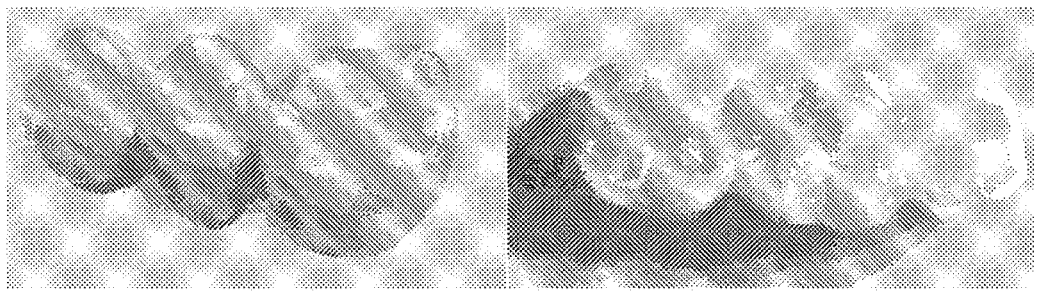
FIG. 9a is a photograph of a dental all-ceramic restoration produced by the commonly used CAD/CAM technology.
FIG. 9b is a photograph of a dental all-ceramic restoration produced by wet-forming according to the present invention.
Figures 9C, 9D:
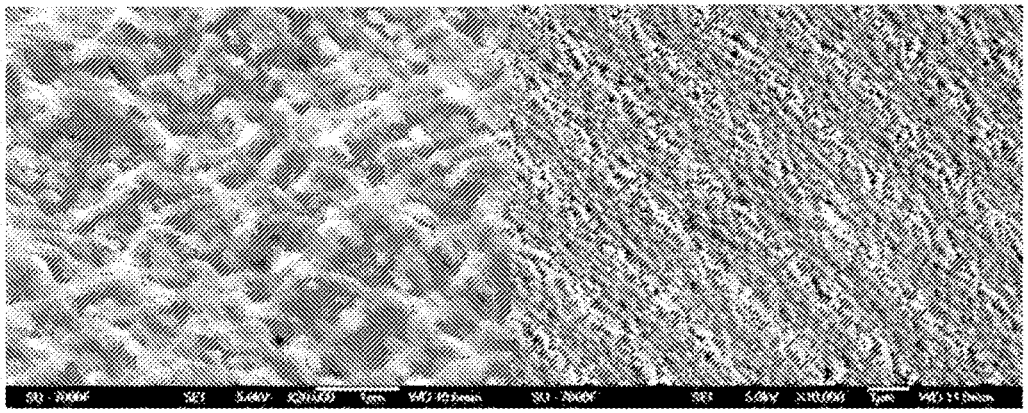
FIG. 9c is a scanning electron micrograph of the surface of the dental all-ceramic restoration produced by the commonly used CAD/CAM technology manufacturing method.
FIG. 9d is a scanning electron micrograph of the surface of the dental all-ceramic restoration produced by wet-forming according to the present invention.

The results were shown in FIG. 9. FIG. 9a shows the dental zirconia all-ceramic restoration produced by the prior art. The surface had visible marks remaining from the removal of the connecting bars and local grinding traces (the sample has been partially polished). This restoration was not smooth enough to be applied in clinic and needs to be further polished. FIG. 9b shows the dental zirconia all-ceramic restoration produced by the wet-forming of the present invention. The outer surface of the dental all-ceramic restorations had neither visible marks remaining from the removal of the connecting bars nor local grinding traces and chipping, and was smooth with uniform structure. FIG. 9c shows the microstructure of the dental zirconia all-ceramic restoration produced according to the prior art. The particles packing on the surface was inhomogeneous, uneven and rough. FIG. 9d shows the microstructure of the dental zirconia all-ceramic restoration produced by the wet-forming of the present invention. The particles packing on the surface was homogeneous, even and smooth.

The above-described embodiments are merely preferred embodiments of the present invention, and are not to be construed as being limited thereto. Other variations and modifications are possible without departing from the technical scope of the claims.

That which is claimed:

1. The manufacturing method of a dental all-ceramic restoration comprising the steps of:
   step (1): milling a mould blank to obtain a cavity mould having an inner surface corresponding to an outer surface form of a digital wax pattern, or a convex mould having an outer surface corresponding to an inner surface form of the digital wax pattern;
   step (2): injecting a ceramic colloid into the cavity mould, or sealing the convex mould with a matched sleeve and then injecting the ceramic colloid into a shaping cavity between the sleeve and the convex mould, wherein after being dried, a hardened ceramic green body with less than 10% liquid phase content is formed;
   step (3): according to the inner surface form of the digital wax pattern, the outer surface form of the digital wax pattern, or the inner surface form combined with a partial outer surface of the digital wax pattern below a height of contour, milling the hardened ceramic green body to obtain a dental all-ceramic restoration body with the same form as the digital wax pattern;
   wherein connecting bars are not used to connect the dental all-ceramic restoration body with the surrounding mould blank during the milling operation,
      wherein before step (1) the manufacturing method further comprises the steps of:
      Step A: tooth preparation;
      Step B: making optical models of a prepared tooth;
      Step C: generating the digital wax pattern of the dental all-ceramic restoration according to the optical models obtained in step B as the data source;
   and wherein
      after step (3) the manufacturing method further comprises the steps of:
      Step D: removing the dental all-ceramic restoration body;
      Step E: sintering the body thereof in a sintering furnace to form the dental all-ceramic restoration;
      wherein, within the step A, the tooth preparation is carried out according to dental preparation principles for all-ceramic restorations; within the step B, the optical models of the prepared tooth include at least the prepared tooth, adjacent teeth on each side of a mouth and opposite teeth; within the step C, the digital wax pattern of the dental all-ceramic restoration is designed by dental restorative design software; within the step D, the method of removing the dental all-ceramic restoration body is to mill away surrounding material of the mould blank to create a gap and then to directly take the body out by clamping or negative-pressure suction; within the step E, a sintering temperature is ranging from 1300° C. to 1600° C. with a holding time ranging from 0.1 h to 3 h.

2. The manufacturing method of claim 1, wherein the cavity mould of step (1) has an inner surface corresponding to a complete outer surface form of digital wax pattern or corresponding to a partial outer surface form of digital wax pattern, wherein, in step 1 during manufacturing the cavity mould having the partial outer surface form of digital wax pattern, a part between the height of contour and incisal edge of anterior tooth or occlusal surface of posterior tooth, is milled according to the outer surface form of digital wax pattern, whereas an other part between the height of contour and cervical margin is milled along a vertical line of the height of contour to mould blank without producing an undercut form below the height of contour.

3. The manufacturing method of claim 1, wherein the material of the mould blank is one or a mixture of a plurality of the materials selected from the group consisting of gypsum, paraffin, epoxy, and polyethylene; and wherein a porosity of the mould blank is 0% to 60%.

4. The manufacturing method of claim 3, wherein the porosity of the mould blank is 0% to 40%.

5. The manufacturing method of claim 1, wherein the ceramic colloid comprises a solid phase component and a liquid phase component, and wherein the solid phase component accounts for 20% to 60% by volume and the liquid phase component is water, alcohols, or their mixture.

6. The manufacturing method of claim 5, wherein the solid phase component is one or a mixture of a plurality of the ceramics selected from the group consisting of alumina, zirconia, spinel, garnet, and mullite.

7. The manufacturing method of claim 6, wherein the solid phase component is the mixture of 5% spinel and 95% zirconia, the mixture of 20% zirconia and 80% alumina, the mixture of 10% spinel and 90% alumina, or the mixture of 95% zirconia and 5% alumina, by weight.

8. The manufacturing method of claim 1, wherein the method is for manufacturing a plurality of dental all-ceramic restorations, and wherein a plurality of bodies of the plurality of dental all-ceramic restoration are manufactured simultaneously from a single mould blank and a single hardened ceramic green body according to steps (1) to (3).

9. The manufacturing method of a dental all-ceramic restoration comprising the steps of:
- step (1) milling a mould blank to obtain a cavity mould having an inner surface corresponding to an outer surface form of a digital wax pattern, or a convex mould having an outer surface corresponding to an inner surface form of the digital wax pattern;
- step (2) injecting a ceramic colloid into the cavity mould formed in step 1, wherein after being dried, a hardened ceramic green body with less than 10% liquid phase content is formed; or sealing the convex mould formed in step 1 with a matched sleeve and then injecting the ceramic colloid into a shaping cavity between the sleeve and the convex mould, wherein after being dried, a hardened ceramic green body with less than 10% liquid phase content is formed;
- step (3) according to the inner surface form of the digital wax pattern, or the inner surface form combined with a partial outer surface of the digital wax pattern below a height of contour, milling the hardened ceramic green body formed in the cavity mould to produce a dental all-ceramic restoration body with the same form as the digital wax pattern; or according to the outer surface form of the digital wax pattern, milling the hardened ceramic green body formed in the convex mould shaping cavity to produce the dental all-ceramic restoration body with the same form as the digital wax pattern;

wherein connecting bars are not used to connect the dental all-ceramic restoration body with the surrounding mould blank during the milling operation, wherein before step (1) the manufacturing method further comprises the steps of:
Step A: tooth preparation;
Step B: making optical models of a prepared tooth;
Step C: generating the digital wax pattern of the dental all-ceramic restoration according to the optical models obtained in step B as the data source;

and wherein
after step (3) the manufacturing method further comprises the steps of:
Step D: removing the dental all-ceramic restoration body;
Step E: sintering the body thereof in a sintering furnace to form the dental all-ceramic restoration;

wherein, within the step A, the tooth preparation is carried out according to dental preparation principles for all-ceramic restorations; within the step B, the optical models of the prepared tooth include at least the prepared tooth, adjacent teeth on each side of a mouth and opposite teeth; within the step C, the digital wax pattern of the dental all-ceramic restoration is designed by dental restorative design software; within the step D, the method of removing the dental all-ceramic restoration body is to mill away surrounding material of the mould blank to create a gap and then to directly take the body out by clamping or negative-pressure suction; within the step E, a sintering temperature is ranging from 1300° C. to 1600° C. with a holding time ranging from 0.1 h to 3 h.

10. The manufacturing method of claim 9, wherein the method is for manufacturing a plurality of dental all-ceramic restorations, and wherein a plurality of bodies of the plurality of dental all-ceramic restorations are manufactured simultaneously from a single mould blank and a single hardened ceramic green body according to steps (1) to (3).

* * * * *